United States Patent [19]
Richardson

[11] Patent Number: 5,697,165
[45] Date of Patent: Dec. 16, 1997

[54] SYSTEM FOR MEASURING STIFFNESS OF A FRACTURED BONE

[76] Inventor: James Bruce Richardson, Westminster House, Old Chirk Road, Gobowen, Oswestry, Shropshire SY11 3LW, United Kingdom

[21] Appl. No.: 574,204

[22] Filed: Dec. 18, 1995

[30] Foreign Application Priority Data

Jun. 20, 1994 [GB] United Kingdom .................. 9412321

[51] Int. Cl.$^6$ ................................................. A61B 5/103
[52] U.S. Cl. ............................................. 33/512; 128/782
[58] Field of Search ..................................... 33/1 N, 1 PT, 33/347, 511, 512, 515, 534, 645, 806; 128/774, 782

[56] References Cited

U.S. PATENT DOCUMENTS

| | | | |
|---|---|---|---|
| 1,590,499 | 6/1926 | Cozad | 33/512 |
| 2,267,157 | 12/1941 | Lippincott | 33/512 |
| 4,327,591 | 5/1982 | Dybel | 73/855 |
| 4,771,548 | 9/1988 | Donnery | 33/1 N |
| 4,846,194 | 7/1989 | Sabia | 33/512 |
| 5,339,533 | 8/1994 | Richardson | 33/512 |
| 5,457,891 | 10/1995 | Taylor | 33/534 |
| 5,493,788 | 2/1996 | Richardson | 128/782 |

FOREIGN PATENT DOCUMENTS

| | | |
|---|---|---|
| 0177270 | 4/1986 | European Pat. Off. . |
| 0324279 | 7/1989 | European Pat. Off. . |
| 0357966 | 3/1990 | European Pat. Off. . |
| 0420430 | 4/1991 | European Pat. Off. . |
| 0458486 | 11/1991 | European Pat. Off. . |
| 0519568 | 12/1992 | European Pat. Off. . |
| 2200457 | 3/1988 | United Kingdom . |
| WO 8601588 | 3/1986 | WIPO . |

OTHER PUBLICATIONS

Patent Cooperation Treaty International Search Report, Intl. App. No. PCT/GB95/04138, Intl Filing Date: 19 Jun. 1995, Priority Date: 20 Jun. 1994, Applicant: James Bruce Richardson.

Cunningham et al., *Eng. Med.*, vol. 16, No. 4, 1987, pp. 229–232.

Bourgois, Journal A, vol. 24, No. 3, 1983, pp. 139–153.

James et al., Eng. Med., vol. 11, No. 3, 1982, pp. 123–124.

Biometrics, "Instrumentation for the data acquisition and analysis of human activity". (no date).

Biometrics, "Computer Games Get Physical" (no date).

Kenwright, et al., Journal of Bone and Joint Surgery, vol. 73–B, No. 4, 1991, pp. 654–659.

*Primary Examiner*—G. Bradley Bennett
*Attorney, Agent, or Firm*—Hopgood, Calimafde, Kalil & Judlowe

[57] ABSTRACT

A set or kit of readily assembled components for measuring bone stiffness as in the case of a fractured tibia in the course of healing repair. The components comprise a unit-handling elongate stiff bar with an independent pivotally suspended footing element at each end of the bar, a goniometer having means for movably securing its respective ends to the respective footing elements, a light-weight load cell, and a small computer package, adapted to continuously respond to the outputs of the load cell and of the goniometer and to display and/or record (i.e., store) measured stiffness data. In a preferred embodiment, a level-responsive device, such as an air-bubble sight, is fixed to the bar to facilitate and to enhance the accuracy of bone-stiffness measurement, in that the level indicator can assure use for measurements wherein the pivot axis of each footing suspension is truly horizontally oriented.

12 Claims, 2 Drawing Sheets

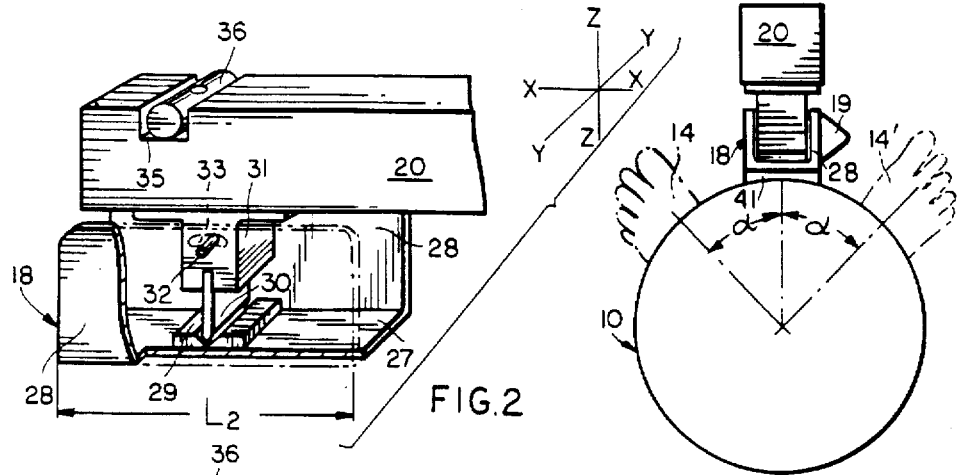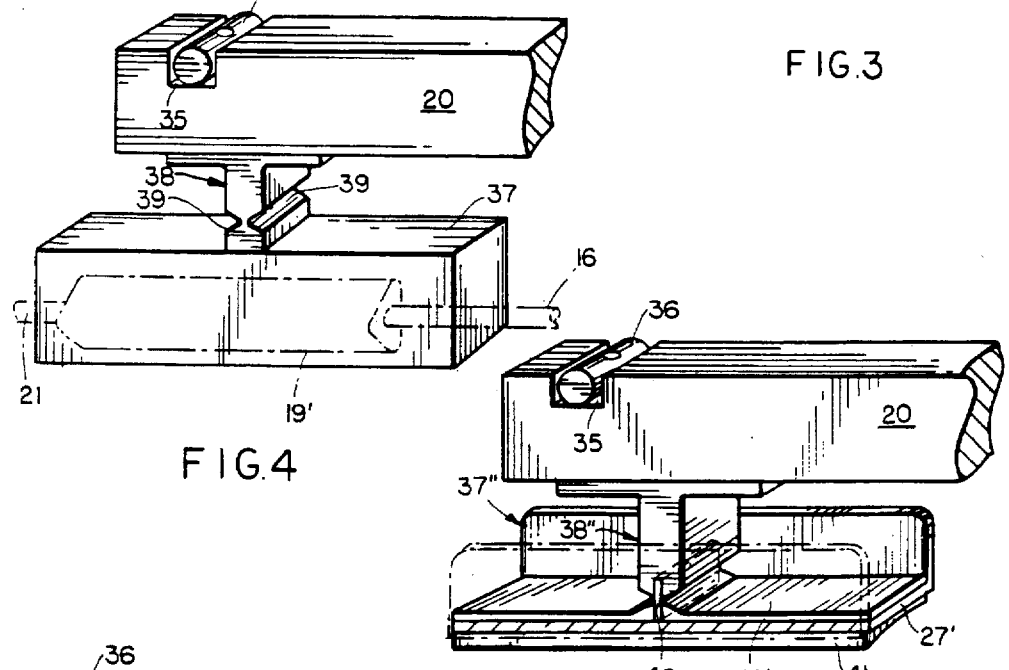

SYSTEM FOR MEASURING STIFFNESS OF A FRACTURED BONE

BACKGROUND OF THE INVENTION

The invention relates to apparatus for measuring stiffness of a fractured bone in the course of bone healing, wherein the healing has been aided by a cast for retention of the broken fragments.

To date much of the clinical data and research on bone-fracture healing has been in the circumstance of external fixation of a broken tibia; the tibia has been the source of such measurements because of the frequency of tibia fracture and the need to restore weight-bearing capability at the repaired site. Thus, in the present discussion, the tibia will be considered illustratively, since principles applicable to the tibia are applicable to other bones in the course of fracture repair.

The paper entitled: "The Measurement of Stiffness of Fractures Treated With External Fixation", Cunningham, et al., *Engineering in Medicine*, Vol. 16, No. 4, 1987, describes apparatus and a technique for indirectly measuring fracture stiffness, periodically in the course of healing a fractured tibia, wherein the patient is seated and rests the heel of his broken limb on a load cell so that the fractured bone, including its external fixator, are otherwise unsupported. The fixator is equipped with a transducer which is able to measure bending as a function of vertically downward force application to the leg. This technique has the disadvantage that even if bone-screw anchorages retain their fidelity, the deflection measurement must include a correctional calculation which reflects the fact that primary stiffness is in the fixator. Bone-stiffness measurement is thus indirect, and as a practical matter, the need to stress the bone in order to stress the fixator is the occasion for progressive deterioration of the effectiveness of bone-screw anchorage, resulting in progressive loss of measurement accuracy. To forestall the loss of bone-screw anchorage, one must severely limit the number and frequency of such measurements.

Published European Patent Application A0,324,279 describes apparatus for direct measurement of bone stiffness in circumstances generally similar to those of the Cunningham, et al. article, except that for purposes of making the deflection measurement, the fixator used for aiding fracture repair is temporarily removed, leaving fixator-bone screws in place; and brackets releasably clamped to the bone screws provide proximal and distal points of support for the respective end mounts of a flexible elongate goniometer. The goniometer is the only external connection between the bone stubs on longitudinally opposite sides of the fracture, and therefore deflections measured for the vertically downward force applied to the limb at the fracture site are direct measurements, requiring no compensating calculation for fixator or goniometer stiffness, because the goniometer structure is inherently flexible and limp, and of negligible stiffness.

Despite the potential for direct measurement afforded by the structure of said published European patent application, the apparatus is structurally relatively crude, and therefore repeatability of measurements at any given occasion is somewhat open to chance, particularly in respect of desired alignment and orientation of the mounting ends of the goniometer, with respect to each other and with respect to the fractured bone. The relatively crude nature of the apparatus disclosed in said published European patent application also applies to an embodiment wherein there has been no external fixation, and wherein spaced mounts for the respective ends of the goniometer are merely strapped to the patient's leg, at spaced proximal and distal offset from the region of fracture.

U.S. patent application Ser. No. 08/163,426, filed Dec. 8, 1993, now U.S. Pat. No. 5,339,533 describes an improved apparatus wherein bone stiffness is evaluated in the course of fracture repair, using goniometer-mounting clamps to bone screws after removal of an external fixator, and wherein adjustments for accurate orientation of the goniometer mounts are greatly aided by use of a level indicator at each of the two goniometer mounts.

A need exists for greater simplicity in apparatus of the character indicated, particularly for bone-fracture cases that have been relying upon a plaster or other cast, wherein of course removal of the cast exposes only the afflicted limb, and no bone screws from which to derive goniometer mounting.

BRIEF STATEMENT OF THE INVENTION

It is an object of the invention to provide improved apparatus for making bone-stiffness measurements of the character indicated.

A specific object is to provide apparatus meeting the above object and featuring repeatable accuracy and consistency of stiffness measurements to a degree that has previously been unavailable.

Another specific object is to meet the above objects with apparatus lending itself to ready assembly and disassembly, without requiring specialized tooling, and sufficiently portable when disassembled to allow the orthopedic specialist to carry, in a light-weight case, all components needed to assemble, use and disassemble the apparatus at each of a relatively large plurality of patient locations in a single day of varied bone-stiffness measurement visits.

A further specific object is to meet the above objects with apparatus which does not require clamping to any part of a patient's fractured limb.

It is also an object to provide hand-held apparatus meeting the above objects and enabling single-handed application to the fractured limb throughout a given course of bone-stiffness measurement.

The invention achieves these objects by providing a set or kit of readily assembled components, namely: a unit-handling elongate stiff bar with an independent pivotally suspended footing element at each end of the bar, a goniometer having means for movably securing its respective ends to the respective footing elements, a light-weight load cell, and a small computer package, adapted to continuously respond to the outputs of the load cell and of the goniometer and to display and/or record (i.e., store) measured stiffness data in a preferred embodiment, a level-responsive device, such as an air-bubble sight, is fixed to the bar to facilitate and to enhance the accuracy of bone-stiffness measurements, in that the level indicator can assure use for measurements wherein the pivot axis of each footing suspension is truly horizontally oriented.

BRIEF DESCRIPTION OF THE DRAWINGS

Preferred embodiments of the invention will be described in detail, in conjunction with the accompanying drawings, in which:

FIG. 2 is an enlarged fragmentary perspective view, partly broken away and in section,. showing a suspension detail of the structure of FIG. 1;

FIG. 3 is an end view of the device of FIG. 1, in the context of use on the patient's left leg, with the patient's foot oriented at an angle α to the vertical;

FIG. 4 is a view generally similar to FIG. 2, to show a first modification;

FIG. 5 is another view similar to FIG. 2, for a second modification; and

FIG. 6 is a further view similar to FIG. 2, for a third modification.

DETAILED DESCRIPTION

Figure 1:
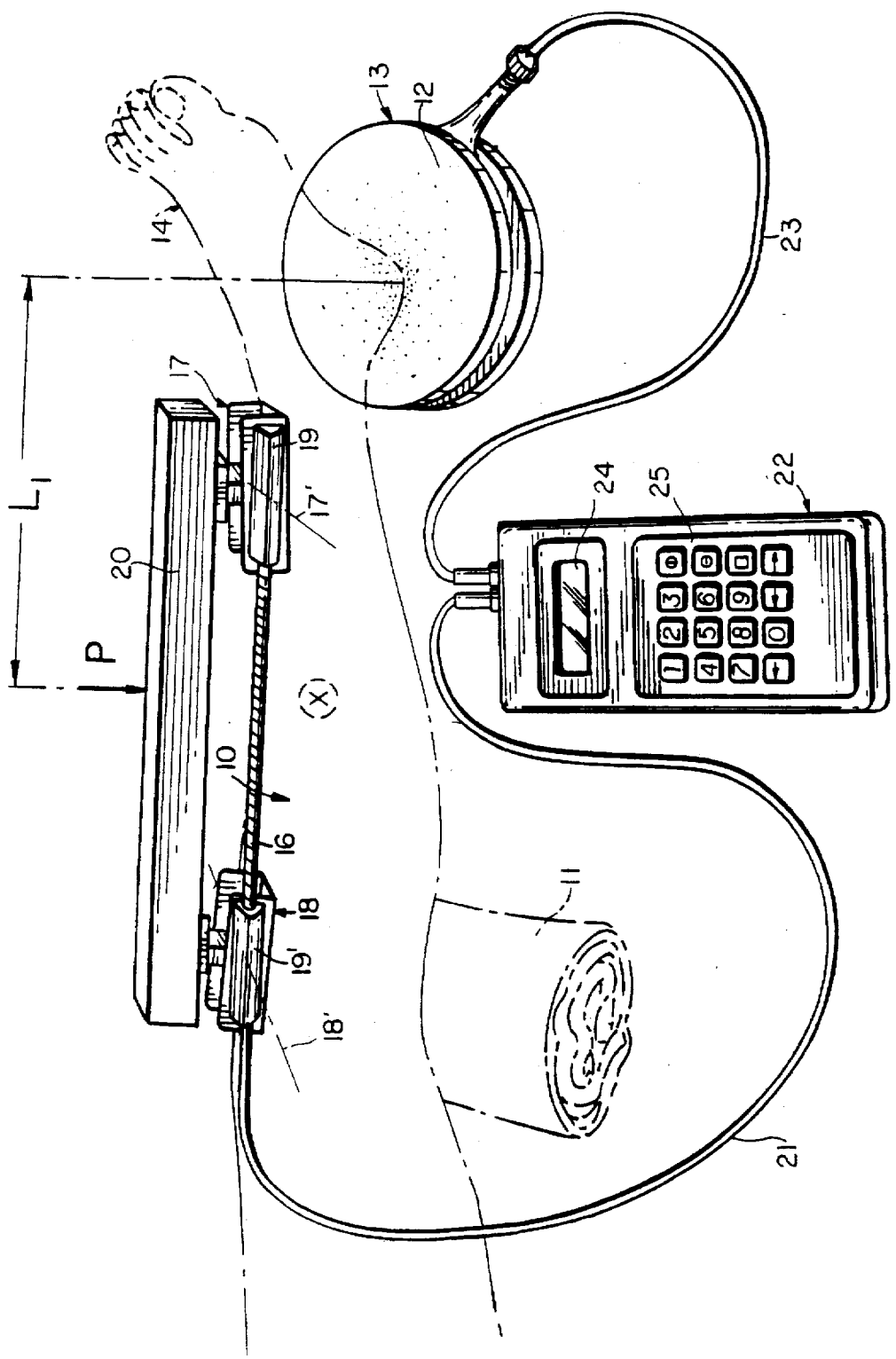
FIG. 1 is a simplified view in perspective, for the case of a bone-stiffness measuring device of the invention, in application to a patient having a fractured tibia at generally the location ⓧ in the drawing.

In the diagram of FIG. 1, the mark Ⓧ generally designates the location of a tibia fracture in the left leg 10 of a patient who has experienced a normal and illustrative period of at least eight weeks following surgery wherein the leg has been retained in a cast. At the juncture of interest, the cast has been removed for inspection and measurement of the strength of the fractured bone.

The patient may be lying flat in bed or seated on a bench, with his knee supported as by a tight roll 11 of towelling and his heel supported by the upper plate 12 of a load cell 13. The span between his points of heel and knee support is otherwise unsupported, the orientation of the left foot 14 being, in the form shown (FIG. 3, heavy phantom), generally upright but inclined at an angle α away from a geometric plane that includes the axis of the tibia and which substantially vertically orients a normal to the broad anterior surface of the tibia. Suitably, the angle α is about 45 degrees. It is noted that this orientation brings the patient's adjacent fibula into the generally horizontal plane of the tibia, and that whether the fibula is or is not also fractured, the fibula is relatively flexible and therefore has inconsequential effect on vertical deflections involved in measuring tibia stiffness. In measuring tibia stiffness in the right leg, FIG. 3 further shows (in light phantom) the right foot 14' similarly but oppositely oriented at angle α away from the vertical plane, to an image position with respect to orientation of the left foot 14.

Briefly, the apparatus to perform the stiffness measurement comprises an elongate goniometer 16 mounted to distal and proximal footing elements 17, 18, each of which is connected in unit-handling relation to an elongate bar 20. The connection of each of the footing elements 17, 18 to bar 20 is one of pivotal or floating suspension about an axis transverse to the elongate direction of bar 20. In FIG. 1, the pivotal-suspension axes for the respective footing elements 17, 18 are schematically indicated at 17', 18'; these axes are parallel and should be horizontal when measurements are made. Detail for the footing elements and their effective floating connection to bar 20 is provided below for several embodiments in connection with FIGS. 2, 4, 5 and 6. The goniometer 16 has distal and proximal end mounts 19, 19' of generally triangular-prismatic appearance, and the base face of each of these end mounts is removably attachable to a vertical side wall of one of the footing elements 17, 18, once the bar 20 and its footing elements have been brought to bear against the patient's leg in near adjacency to the broad anterior shin (tibia) surface, in which case the respective footing elements 17, 18 will be understood to have self-adapted (about the respective axes 17', 18') to the local slope of the anterior surface of the tibia.

The presently preferred goniometer, for which the triangular section (shown at 19 in FIG. 3) is applicable, is one of the "Electrogoniometer" products of Penny & Giles Biometrics Ltd., of Blackwood, Gwent, Wales. Their electrogoniometers include single-axis, twin-axis and torsionally sensitive devices, of which the single-axis variety is satisfactory and preferred for purposes of the present invention, in that the requisite bending for a stiffness measurement of the tibia of leg 10 is desirably in a single-vertical plane, namely, the sagittal plane of the tibia of leg 10. It suffices to observe that the indicated single-axis goniometer comprises an elongate flat flexible strip of suitable plastic substrate material having strain-gage resistance wire or coating applied to its upper and lower surfaces, for inclusion in an electrical bridge circuit, which is resistance-sensitive to bending in the vertical plane. The end mount 19' which accommodates cable 21 is the end at which the proximal end of the goniometer strip is fixed. A closely wound coil of flexible, softly compliant wire is fixed at its proximal end to end mount 18 and at its distal end to end mount 17; this coil provides mechanical protection of the goniometer strip, which is freely guided by and within the flexible coil, the distal end of the goniometer strip being free of connection to and therefore slidably guided within the distal end mount 19.

Goniometer 16 is shown to produce an electrical-signal output, via a flexible multi-conductor cable 21, to a battery-operated microcomputer unit 22 which is also supplied by an electrical-signal output in a second cable 23, from load cell 13. The microcomputer will be understood to be programmed for the calculation and display at 24 of instantaneously measured bending moment, preferably in Newton-meters per degree of bone-bending deflection, in response to the physician's central application of downward force P to bar 20, thereby inducing vertically downward bending deflection of the tibia fracture at Ⓧ; alternatively, the physician may choose to induce bending deflection of the tibia fracture in response to his careful application of pressure P directly to the leg, as via the cupped palm of his other hand, while maintaining the footing elements in such sufficiently loaded contact with the leg as to assure floating action of the footing elements. In the course of bending deflection of the fractured tibia, the calculation is performed pursuant to the two cable input signals, with dimensional factors, such as the horizontal distance $L_1$ from the patient's heel to his fracture site Ⓧ entered into the computer 22 via a push-button array panel 25, shown on the face of the computer.

More specifically, FIG. 2 illustrates supporting structure for the proximal footing element 18, which will be understood to be identical to the distal footing element 17. Element 18 is seen in FIG. 2 to comprise an upwardly open channel of longitudinal extent $L_2$ and having a flat base 27 and spaced upstanding side plates 28. A hard fulcrum plate 29 is fixed to base 27 and establishes a transverse groove which provides supporting engagement for a knife blade 30 fixed to a blade mount 31 that is in turn fixed to the underside of bar 20. A transverse pin 32 fixed to and projecting laterally through arcuate side-plate slots, as suggested at 33 for the near plate 28 in FIG. 2, retains footing element 18 in permanent assembly to bar 20, while permitting a measure of floating tilt of element 18 with respect to bar 20 when applied to the leg. In FIG. 1, for illustrative purposes, opposite directions of such floating tilt are shown for each of the respective footing elements, and it will be understood that prior to application of force P to bar 20 or to the leg, the respective goniometer-end mounts 19, 19' will have been removably applied to one of the side plates 28 of each of the footing elements 17, 18, thus accounting for the straight and continuously aligned disposition of the goniometer 16 and its mounts 19, 19', as shown in FIG. 1. The removable mounting of the goniometer end mounts 19, 19' to the respective side plates may be via use of double-stick tape, or coating laminations of hook-and-loop materials, on the respective surfaces to be removably engaged.

For the indicated goniometer, the end-mount cross-sections are isosceles-triangular, with a flat base that must be vertical, in order to orient the goniometer strip for response to bending in the vertical plane. To assure such orientation, the side plates 28 of each of two duplicate mounts 19, 19' are flat and vertically oriented, as best seen in FIG. 3; and in a three-axis directional legend of FIG. 2, X identifies the generally horizontal, longitudinal direction parallel to the axis of the shin bone (tibia) of leg 10, Y identifies the strictly horizontal direction orthogonal to the X direction, and Z is the vertical direction, preferably strictly perpendicular to the Y-axis direction and generally perpendicular to the longitudinal direction X. FIG. 2 also shows bar 20' to have been milled out across its upper surface and in the transverse or Y direction, to establish a local groove 35 which provides fixed seating support and location for a so-called spirit level 36, having an upwardly exposed air-bubble indicator. Thus, as long as the air bubble of the spirit level remains centered, it may be known that the goniometer strip is correctly oriented for electrical response to bending in the vertical plane. The groove (35) location for spirit-level indicator 36 is preferably outboard of the span between longitudinal locations of pivotal (i.e., floating) support of the respective footing elements 17, 18.

In the embodiment of FIG. 4, the proximal footing element 37 is an elongate rectangular prismatic block of length ($L_2$) as in FIG. 2, but permanently united in unit-handling relation with bar 20' via a one-piece mount 38 which has been so weakened by opposed transverse grooves 39 as to enable floating flexure about the Y-axis direction when bubble sight 36 indicates horizontal orientation of the Y-axis of flexure. A similar mount (38) for a duplicate of footing element 37 at the distal end of bar 20 will be understood.

In the embodiment of FIG. 5, the mount 38' for footing element 37' is again of integral nature, with opposed grooves establishing a weakened location 39' of floating flexure about the Y-axis direction, but at a preferred level which is much more close to the plane of footing-element contact with leg 10. To this end, footing element 37' is an upwardly open channel, and the base 40 of mount 38' is elongate to distribute loading force along the bottom panel 27' of the channel. A thin pad 41 of resilient material lines the underside of channel 37' for patient comfort and is seen in FIG. 3 to be of shallow concave cylindrically arcuate nature.

In the embodiment of FIG. 6, the mount 38" also provides a lowered location of Y-axis flexure, by using a vertically oriented thin strip 42 of flexible metal such as stainless steel which has been embedded along its upper and lower ends, in supporting vertical grooves of the mount 38", wherein the base-end support is derived from two base elements 40' which line the bottom panel of channel 37".

USE OF THE INVENTION

1. The patient is made comfortable either in the seated position mentioned above, or lying flat on a firm bed. The patella and the foot should be facing upwards, with such rotation of the foot at angle α as to place the fibula in the same horizontal plane as the tibia. The proximal end of the tibia is rested on a suitable support, as on the roll of towelling 11, or on a small sand bag from an operating theater. The load cell 13 is placed under the heel, such that the cell is secure, with the heel centered on the top plate 12. The tibia should be supported only at each end, leaving the intervening length unsupported and suspended, without touching the bed or anything else.

2. The number of weeks since fracture should be confirmed with the patient. The cast should not be removed short of eight weeks after injury, unless the surgeon has every confidence that the fracture will be stable.

3. The surgeon can then grasp bar 20 and gently apply it to leg 10 such that each of the footing elements 17, 18 adopts its own respective local conformance to longitudinally distal and proximal offsets from the fracture, taking care to achieve an indicated transverse horizontal at 36. Then, while holding this gentle application with one hand, and visually sighting for alignment, apply the distal goniometer mount 19 to its footing element 17, such that its elongate direction is generally aligned with the proximal footing element 18, before applying the proximal goniometer element 19' to the proximal footing element 18. Having thus preliminarily fixed the positions and orientation of goniometer end-mount support and orientation, and after sighting along the flat base surface of the triangular section of mounts 19, 19' in succession, for sagittal-plane alignment with the tibia, the goniometer should be finally secured at its proximal and distal end mounts, under slight tension of the protective wire coil, thus avoiding goniometer droop between its supported ends. This slight tension does not tense the goniometer, but it is a means of avoiding play in the event of slack in the wire coil. The spirit level 36 associated with bar 20 and therefore also with each of the proximal and distal mounts of the goniometer, coupled with the sagittal-plane adjustment mentioned above, assures that the goniometer is in the correct plane when the spirit level registers horizontal. But it is noted that if the goniometer is not directly over the tibia, it is possible that some rotation may occur at the fracture site, resulting in an erroneous stiffness measurement. Any rotation that occurs with the goniometer in the correct position will not be registered, because the rotation will be in the frontal plane; the goniometer will only register changes in the sagittal plane.

4. If the cables 21 and 23 from the goniometer and from the load cell have not previously been connected to the microcomputer 22, these connections should now be made, and the microcomputer should be switched on. As noted above, bone stiffness is measured as angular change, per unit load, with a length factor $L_1$ reflecting distance from the measured load to the nearest point of weakness. The microcomputer 22 is programmed to compute and display bone stiffness, in Newton-meters per degree, pursuant to the formula:

$$\text{STIFFNESS} = \frac{\text{FORCE} \times \text{DISTANCE } (L_1)}{\text{ANGULAR DISPLACEMENT}}$$

Strictly speaking, the measured displacement should be linear, but since required angular measurement is small (<1°), measurement of angular displacement with a sensitive goniometer element of fixed length (as here) is inconsequentially different from a linear measurement of displacement.

5. It should be noted that when the area of bone weakness is not linear and transverse, the distance $L_1$ entered at 22 should be the shortest distance from the heel to the area of bone weakness; this is to avoid a stiffness measurement that is artificially high. If the fracture is a segmental one, the measurement of $L_1$ is to the most distal fracture.

6. Having set the apparatus and the patient for a stiffness measurement, the presently preferred programmed succession of events is as follows, all while manually holding bar 20 to leg 10 and with a correctly indicated level at 36:

(a) The first measurement is a test measurement, to confirm that the patient is comfortable.

(b) The start button at 25 is pressed to initiate the measurement.

(c) There is a short programmed delay to allow the surgeon to place his other hand on the tibia over the fracture, or to make sure of his correct readiness to apply vertically downward force via bar 20. The longitudinal position of the hand or of the grasp of bar 20 is not critical, as long as it is between the two footing elements 17, 18.

(d) At a first programmed beep from the microcomputer, the surgeon starts to press on the leg, directly or via bar 20. The object is to bend the bone between 0.5 and 1.0 degrees. If the stiffness is low, and the bone is in the early stages of healing, the pressure required will be slight. As the stiffness increases, the pressure will have to increase also, but it will be no more than the pressure that is required for a clinical assessment of healing. The numerical display at 24 will be an indication of the changing angle with a target change of 0.5°, and the microcomputer is programmed to sound an alarm if 1.0° is exceeded. The measurement is taken over a period of three seconds, and the aim should be to apply a steadily increasing pressure over this period of time, so that the angle can be observed to change throughout the test. Sudden movements should be avoided. The downward pressure is removed after a second programmed beep is heard; this will be three seconds after the first beep.

(e) While performing the test measurement, the surgeon should watch the patient's face for signs of discomfort. A common fault for surgeons new to the technique is not to press hard enough. If the angle achieved is less than 0.5°, a repeat test measurement is requested, by programmed display at 24.

(f) If the test is satisfactory, the surgeon proceeds to perform five measurement procedures. If the patient and surgeon are confident with the procedure, then the surgeon can observe the change in angulation during the test to confirm that it is adequate.

(g) While the measurement is being performed, the microcomputer program correlates the change in angle with the change in load. This correlation is displayed as a coefficient with the stiffness measurement, and the surgeon has the opportunity to accept or reject each reading according to the correlation. In addition, the program will automatically reject any test with a coefficient of less than 0.900. With practice, it is possible for the surgeon to achieve correlations greater than 0.950, and this should be the aim.

(h) After five successive measurements, the microcomputer program provides a display at 24 of the average of the five readings. This average is the bone stiffness.

(i) If the result is less than 15 Nm/degree, the leg 10 is again placed in a cast. If the result is more than 15 Nm/degree, a decision should be made as to whether the cast is no longer necessary.

Thus far, use of the described apparatus and technique have been primarily in application to the tibia, be it for stiffness measurement of a healing fracture or of an osteotomy. Use of the femur is also possible but there has been insufficient experience to be able to set a level equivalent to the 15 Nm/degree value indicated above for the tibia.

Use of the apparatus for femur measurements may be briefly summarized by the following procedural steps:

(a) The patient sits on a bed, and the femoral condyles are positioned over the load cell. The cast is removed as for the tibia, and bar 20 is manipulated such that the goniometer is positioned above the femur and in the sagittal plane. The measurement is performed in the same way as for the tibia.

(b) The bar 20 and goniometer 16 are then repositioned, to a lateral position in the frontal plane. The load cell is positioned medial to the condyles, and is held there by the surgeon or an assistant.

(c) The measurement is again performed, but this time with the load applied from the lateral side, to as to press the medial femoral condyle into the load cell.

(d) If x-ray viewing of the configuration of the callus suggests the need, the surgeon can then repeat the stiffness measurement from the medial side, with the load cell and goniometer positions reversed.

SUMMARY

The described stiffness measurement apparatus will be seen to meet all stated objects. The spirit-level location with respect to goniometer-mounting flats enables assurance of the accurate positioning which is needed for high correlation between successive measurements. The surgeon can make an accurate graphical plot of his patient's periodically measured and developing bone repair, enabling enhanced confidence in his decision when to relieve. The patient of retention in a cast, at a time prudently short of development of maximum stiffness in the repairing bone. For example, for the illustrative case of tibia repair, achievement of a measured stiffness of 15 Nm/degree is substantially short of the expected ultimate 50 to 60 Nm/degree stiffness expected of a normal adult; for an overweight patient, a slightly higher target stiffness level of 20 Nm/degree is recommended before relief from fixation in a cast, but this is also snort of the expected ultimate stiffness development.

The described apparatus lends itself not only to enhanced accuracy, and reliability of stiffness measurement, but also to use of a microcomputer 22 programmed as indicated, to complete, within six minutes, a full course of (a) test measurement, (b) five sequential stiffness-measurement cycles, (c) with computer-aided assurance of at least 0.900 correlation, and with an indicated display of the correlation between the five separate measurements, as well as their average, which can be visually observed and/or entered into temporary storage, for later offloading from the microcomputer to the surgeon's patient data bank.

Not the least of the reasons for an ability to complete all measurement tasks in six minutes, is the viewability of spirit level 36 adjacent an exposed portion of the flat upper surface of bar 20, enabling a downward visual sighting which can be readily adjusted for sagittal-plane alignment with the patient's leg.

What is claimed is:

1. As an article of manufacture for use in mounting the respective longitudinal ends of a bending-stress goniometer in an evaluation of the strength of an elongate bone within a limit and in the course of healing subsequent to a regional fracture of the bone, said article comprising:

(a) a rigid elongate bar of length to span the region of fracture with substantial longitudinal overlap of the bone in a zone of proximal offset away from the region of fracture and in a zone of distal offset away from the region of fracture;

(b) first and second elongate footing elements having pivotal suspension from said bar near the respective longitudinal ends of said bar, wherein the pivotal suspension for each of said footing elements provides essentially single-axis pivot action on spaced parallel axes that are in a geometric plane at fixed offset from and parallel to said bar;

(c) one of said footing elements being adapted for development of pivotally floating accommodation to local slope of the limb at limb contact in the zone of proximal offset, and the other of said footing elements being adapted for development of pivotally floating accommodation to the local slope of the limb at limb contact in the zone of distal offset; and (d) means associated with said one footing element for removably mounting one of said goniometer ends, and means associated with said other footing element for removably mounting the other goniometer end.

2. The article of claim 1, wherein said bar and said pivotal suspension and said footing elements are astride a common vertical plane of symmetry which is normal to said pivot axes.

3. The article of claim 1, in which each pivot axis is one of knife-edge contact with a transverse groove in an otherwise flat surface.

4. The article of claim 3, in which the knife-edge for each said contact is a rigid part of said bar and in which the surface for each said contact is a transverse groove in an elongate surface of a footing element.

5. The article of claim 1, in which each of said pivot axes is at substantially the longitudinal midpoint of each footing element.

6. The article of claim 5, in which each of said pivot axes is at greater vertical offset from said bar than from the limb-contact zone of each footing element.

7. The article of claim 1, in which a single rigid body connects each footing element to said bar, and in which the essentially single axis pivot action is produced by each said rigid body being so locally weakened at a single offset from said bar as to provide an independent integral compliant suspension of each footing element from a different end of said bar, wherein compliant action is limited in each case to a different one of the spaced parallel axes.

8. The article of claim 1, wherein said rigid elongate bar carries a level indicator fixed in transverse orientation with respect to the elongate direction of said bar to enable the article to be used when the bar and footing elements are symmetrically aligned in a vertical plane.

9. The article of claim 1, wherein said elongate bar carries a level indicator fixed in an orientation to sense when the pivotal axis of at least one of said suspensions is in a horizontal plane.

10. The article of claim 9, in which said elongate bar has a transverse groove at a longitudinal location which is longitudinally outboard of the longitudinal span between said pivotal suspensions, and in which said level indicator is a bubble sight located and retained in said transverse groove.

11. A kit comprising the article of claim 1, and an elongate goniometer having spaced end mounts each of which mounts is adapted to selective fixation to a different one of said footing elements.

12. The kit of claim 11, additionally including a load cell and a microcomputer, said goniometer producing an electrical output signal in response to bending stress therein and said load cell producing an electrical output signal in response to applied load, and flexible cable means for selective connection of said microcomputer for concurrent response to the output signals of said goniometer and of said load cell.

* * * * *

UNITED STATES PATENT AND TRADEMARK OFFICE
CERTIFICATE OF CORRECTION

PATENT NO. : 5,697,165
DATED      : December 16, 1997
INVENTOR(S): James Bruce RICHARDSON It is certified that error appears in the above-identified patent and that said Letters Patent is hereby corrected as shown below:

Column 1, line 29;   delete "bone-Screw"
                     and insert therefor --bone-screw--

Column 2, line 53;   after "data" insert --.--
                     and change "in" to --In--

Column 3, line 2;    after "section," delete "."

Column 5, line 18;   delete "20'" and
                     insert therefor --20--

Column 5, line 33;   delete "20'" and
                     insert therefor --20--

Column 8, line 30;   after "relieve" delete ". The"
                     and insert therefor --the--

Column 8, line 38;   delete "snort"
                     and insert therefor --short--

Signed and Sealed this

Thirty-first Day of March, 1998

Attest:

BRUCE LEHMAN

Attesting Officer    Commissioner of Patents and Trademarks